(12) United States Patent
Hems et al.

(10) Patent No.: US 8,039,675 B2
(45) Date of Patent: Oct. 18, 2011

(54) CATALYSTS

(75) Inventors: William Patrick Hems, Norwich (GB); Gabriela Alexandra Grasa, Cambridge (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 12/696,736

(22) Filed: Jan. 29, 2010

(65) Prior Publication Data

US 2010/0197976 A1 Aug. 5, 2010

Related U.S. Application Data

(63) Continuation of application No. 10/564,902, filed as application No. PCT/GB2004/002938 on Jul. 7, 2004, now abandoned.

(30) Foreign Application Priority Data

Jul. 15, 2003 (GB) .................. 0316439.9

(51) Int. Cl.
C07C 209/26 (2006.01)
C07F 15/00 (2006.01)
C07F 9/02 (2006.01)

(52) U.S. Cl. .................. 564/489; 548/101; 556/19

(58) Field of Classification Search .................. 564/489; 548/101; 556/19
See application file for complete search history.

(56) References Cited

U.S. PATENT DOCUMENTS

| 6,720,439 B1 | 4/2004 | Ohkuma et al. |
| 2002/0095056 A1 | 7/2002 | Cobley et al. |
| 2003/0045727 A1 | 3/2003 | Nakano et al. |

FOREIGN PATENT DOCUMENTS

| EP | 0 718 265 B1 | 8/2000 |
| EP | 1 134 226 A2 | 9/2001 |
| EP | 1 146 037 A1 | 10/2001 |
| EP | 1 323 724 A2 | 7/2003 |
| EP | 1 134 226 B1 | 1/2007 |
| JP | 11-189558 A | 7/1999 |
| JP | 2002-284790 A | 10/2002 |
| JP | 2003-104993 A | 4/2003 |
| WO | WO-99/24410 A1 | 5/1999 |
| WO | WO-01/58843 A1 | 8/2001 |
| WO | WO-01/74829 A1 | 10/2001 |
| WO | 02055477 | 7/2002 |
| WO | WO-03/048173 A1 | 6/2003 |
| WO | 2004007506 | 1/2004 |

OTHER PUBLICATIONS

Ekkhard Lindner et al., "Supported organometallic complexes Part XXXV. Synthesis, characterization, and catalytic application of a new family of diamine(diphosphine)ruthenium(II) complexes," *Journal of Organometallic Chemistry*, vol. 665 (2003), pp. 176-185.
Takeshi Ohkuma et al., "*trans*-RuH($\eta^1$-BH$_4$)(binap)(1,2-diamine): A Catalyst for Asymmetric Hydrogenation of Simple Ketones under Base-Free Conditions," *J. Am. Chem. Soc.*, vol. 124, No. 23, 2002, pp. 6508-6509.
Janine Cossy et al., "Ruthenium-catalyzed asymmetric reduction of 1,3-diketones using transfer hydrogenation," *Tetrahedron Letters*, vol. 42 (2001), pp. 5005-5007.
Dendukuri Nagamani et al., "Pyrrolidyl Polyamines: Branched, Chiral Polyamine Analogues That Stabilize DNA Duplexes and Triplexes," *Organic Letters*, 2001, vol. 3, No. 1, pp. 103-106.
Ching-Wen Lin et al., "A highly efficient and stereospecific borane reduction of spiro[4.4]nonane-1,6-dione catalyzed by a chiral oxazaborolidine," *Tetrahedron Letters*, vol. 41 (2000), pp. 4425-4429.
Jacqueline S. Barlow et al., "New building blocks for efficient and highly diastereoselective polyol production—synthesis and utility of ($R',R',S,S$) and ($S',S',R,R$)-2,3-butane diacetal protected butane tetrol derivatives," *J. Chem. Soc., Perkin Trans. 1*, 1999, pp. 1627-1629.
George H. P. Roos et al., "Synthesis of novel C$_2$-symmetric ligands based on ($R,R$)- and ($S,S$)- diphenyl-1,3-propanediol," *Tetrahedron: Asymmetry*, vol. 10 (1999), pp. 991-1000.
Takeshi Ohkuma et al., "BINAP/1,4-Diamine—Ruthenium(II) Complexes for Efficient Asymmetric Hydrogenation of 1-Tetralones and Analogues," *Organic Letters*, vol. 6, No. 16, 2004, pp. 2681-2683.

*Primary Examiner* — Joseph Kosack
(74) *Attorney, Agent, or Firm* — RatnerPrestia

(57) ABSTRACT

Catalysts suitable for asymmetric hydrogenation reactions are described comprising the reaction product of a group 8 transition metal compound, a chiral phosphine and a chiral diamine of formula (I)

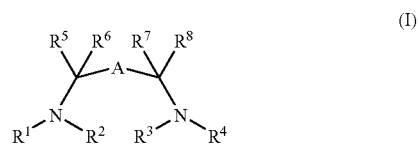

(I)

in which $R^1$, $R^2$, $R^3$ and $R^4$ are independently hydrogen, a saturated or unsaturated alkyl or cycloalkyl group, an aryl group or a urethane or sulphonyl group and $R^5$, $R^6$, $R^7$ and $R^8$ are independently hydrogen, a saturated or unsaturated alkyl or cycloalkyl group, or an aryl group, at least one of $R^1$, $R^2$, $R^3$ and $R^4$ is hydrogen and A is a linking group comprising one or two substituted or unsubstituted carbon atoms.

17 Claims, No Drawings

CATALYSTS

CROSS-REFERENCE TO RELATED APPLICATIONS

This application is a continuation application of U.S. patent application Ser. No. 10/564,902, filed Jun. 15, 2006, now abandoned which is the U.S. National Phase application of PCT International Application No. PCT/GB2004/002938, filed Jul. 7, 2004, and claims priority of British Patent Application No. 0316439.9, filed Jul. 15, 2003, the disclosures of all of which are incorporated herein by reference in their entirety.

FIELD OF THE INVENTION

This invention relates to transition metal catalysts for performing asymmetric hydrogenation reactions and in particular to transition metal catalysts for the asymmetric hydrogenation of ketones and imines.

BACKGROUND OF THE INVENTION

Transition metal catalysts particularly those based on chiral ruthenium (Ru) phosphine complexes are known to be effective for the asymmetric hydrogenation of ketones. EP-B-0718265 describes the use of chiral Ru-bis(phosphine)-1,2-diamine complexes for the hydrogenation of ketones to produce chiral alcohols. Similarly, WO 01/74829 describes a chiral Ru-Phanephos-1,2-diamine complex for the asymmetric hydrogenation of ketones.

Although it is accepted that the combination of bis(phosphine) and the chiral diamine ligands are important for achieving a high enantiomeric excess (ee) and a wide range of phosphine ligands has been described, only 1,2-diamine ligands have been widely used heretofore. By the term "1,2-diamines" we mean diamines wherein the carbon atoms to which the amine functionalities are bound are directly linked. Such diamines include chiral substituted ethylenediamine compounds such as (S,S)-diphenylethylenediamine ((S,S)-Dpen). Without wishing to be bound by any theory we believe that this is due to the perceived need for the resulting conformationally-stable 5-membered ring structure that forms when 1,2-diamines co-ordinate to the metal atom. Larger ring structures, for example those formed using 1,3- or 1,4-diamines can be less conformationally-stable and therefore may be expected to provide catalysts that give lower enantiomeric excesses than the corresponding catalysts prepared using 1,2-diamines.

Accordingly the chiral catalysts used heretofore comprise 1,2-diamines and have relied principally upon variation of the structure of the phosphine ligand to improve their enantioselectivity. Although effective for some substrates such as acetophenone, a range of ketone and imine substrates remain unreactive to the existing catalysts or are obtained with undesirably low enantiomeric excesses.

SUMMARY OF THE INVENTION

We have found surprisingly that chiral catalysts suitable for the hydrogenation of ketones and imines may comprise diamines that provide larger ring structures and that such catalysts can provide higher enantiomeric excesses than those comprising 1,2-diamines.

DETAILED DESCRIPTION OF THE INVENTION

Accordingly the invention provides a chiral catalyst comprising the reaction product of a group 8 transition metal compound a chiral phosphine and a chiral diamine of formula (I)

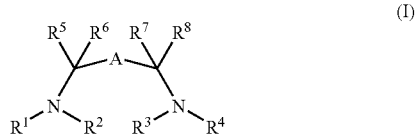

in which $R^1$, $R^2$, $R^3$ or $R^4$ are independently hydrogen, a saturated or unsaturated alkyl, or cycloalkyl group, an aryl group, a urethane or sulphonyl group and $R^5$, $R^6$, $R^7$ or $R^8$ are independently hydrogen, a saturated or unsaturated alkyl or cycloalkyl group, or an aryl group, at least one of $R^1$, $R^2$, $R^3$ or $R^4$ is hydrogen and A is a linking group comprising one or two substituted or unsubstituted carbon atoms.

The group 8 transition metal compound may be a compound of cobalt (Co), nickel (Ni), ruthenium, (Ru), rhodium (Rh), iridium (I), palladium (Pd) or platinum (Pt). For hydrogenation of ketones and imines the transition metal compound is preferably a compound of ruthenium.

The metal compound may be any metal compound that is able to react with the phosphine and the chiral diamine (I) to provide a metal complex catalyst. The metal compound is preferably a metal salt, e.g. halide, carboxylate, sulphonate or phosphonate, or an organometallic compound. Particularly suitable metal compounds include $[RuCl_2(benzene)]_2$ and $[RuCl_2(cymene)]_2$.

The chiral phosphine may be a monodentate or bidentate phosphine. Preferably the chiral phosphine is a chiral bis (phosphine). A range of chiral bis(phosphines) are known and may be used in the present invention. Suitable chiral bis (phosphines) include but are not restricted to the following structural types;

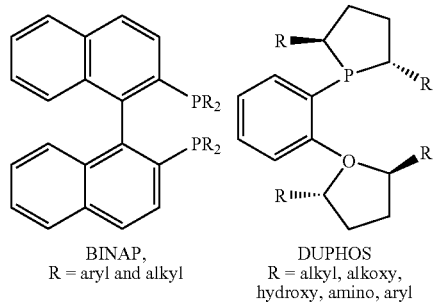

BINAP,
R = aryl and alkyl

DUPHOS
R = alkyl, alkoxy, hydroxy, amino, aryl

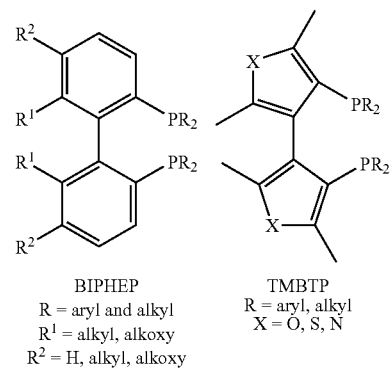

BIPHEP
R = aryl and alkyl
$R^1$ = alkyl, alkoxy
$R^2$ = H, alkyl, alkoxy

TMBTP
R = aryl, alkyl
X = O, S, N

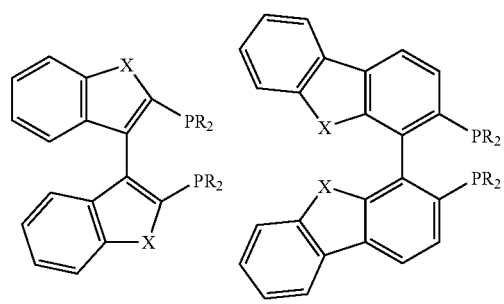
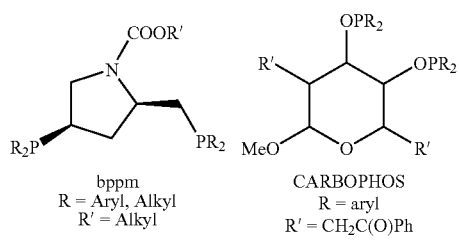
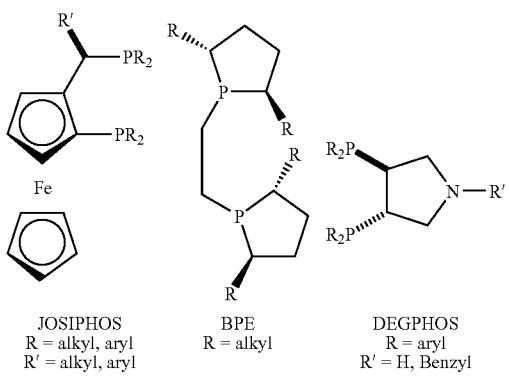
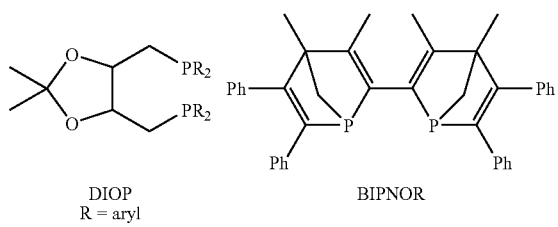
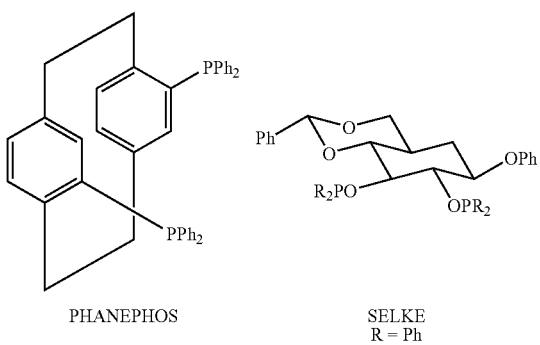
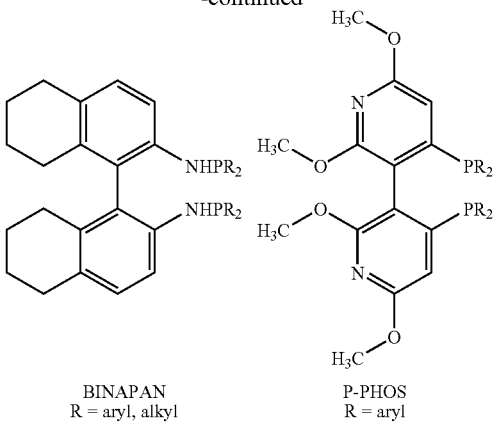

Preferably, the chiral phosphine is based on BINAP, DUPHOS, PHANEPHOS, and P-PHOS, more preferably BINAP where R=Tolyl (tol-BINAP) or P-PHOS where R=Phenyl (P-PHOS), tolyl (tol-P-PHOS) or Xylyl (xyl-P-PHOS) and especially xyl-P-PHOS.

The chiral diamine is of formula (I)

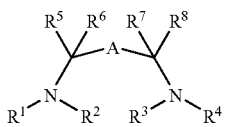

in which $R^1$, $R^2$, $R^3$ or $R^4$ are independently hydrogen, a saturated or unsaturated alkyl, or cycloalkyl group, an aryl group, a urethane or sulphonyl group and $R^5$, $R^6$, $R^7$ or $R^8$ are independently hydrogen, a saturated or unsaturated alkyl or cycloalkyl group, or an aryl group, at least one of $R^1$, $R^2$, $R^3$ or $R^4$ is hydrogen and A is a linking group comprising one or two substituted or unsubstituted carbon atoms.

Alkyl groups may be straight chain or branched alkyl groups (e.g. C1-C20) such as methyl, ethyl, propyl, iso-propyl, butyl, iso-butyl, sec-butyl, tert-butyl, pentyl, hexyl, heptyl, octyl, nonyl, decyl, dodecyl, and stearyl, "cycloalkyl" is meant to encompass (e.g. C3-C10) cycloalkyl groups such as cyclopropyl, cyclobutyl, cyclopentyl, cyclohexyl or adamantyl. Aryl groups may be phenyl (Ph), naphthyl (Np) or anthracyl and heteroaryl groups such as pyridyl. The alkyl groups may be optionally substituted with one or more substituents such as halide (Cl, Br, F or I) or alkoxy groups, e.g. methoxy, ethoxy or propoxy groups. The aryl groups may be optionally substituted with one or more substituent such as halide (Cl, Br, F or I), alkyl (C1-C20) alkoxy (C1-C20), amino ($NR_2$, where R=hydrogen or alkyl), hydroxy, halide (e.g. Cl, Br or F), carboxy ($CO_2R'$, R'=H or alkyl) or sulphonate groups. Suitable substituted aryl groups include 4-methylphenyl (tolyl), 3,5-dimethylphenyl (xylyl), 4-methoxyphenyl and 4-methoxy-3,5-dimethylphenyl.

$R^1$, $R^2$, $R^3$ and $R^4$ may be the same or different and are preferably selected from hydrogen or methyl, ethyl, isopropyl, cyclohexyl, phenyl or 4-methylphenyl groups.

In one embodiment, $R^1$ and $R^2$ are linked or $R^3$ and $R^4$ are linked so as to form a 4 to 7-membered ring structure, preferably a 5- or 6-membered ring structure, incorporating the nitrogen atom.

Most preferably $R^1$, $R^2$, $R^3$, $R^4$ are the same and are hydrogen.

$R^5$, $R^6$, $R^7$ and $R^8$ may be the same or different and are preferably hydrogen, methyl, ethyl, propyl, iso-propyl, butyl, iso-butyl, sec-butyl, tert-butyl, cycloalkyl groups such as cyclohexyl, aryl groups such as substituted or unsubstituted phenyl or naphthyl groups.

In one embodiment one or more of $R^5$, $R^6$ $R^7$ or $R^8$ may form one or more ring structures with the linking group A. The ring structure may comprise an alkyl or heteroalkyl 4- to 7-membered ring, preferably a 5- or 6-membered ring or may be an aromatic ring structure, e.g. aryl or hetero-aryl.

In EP-B-0718265 it was suggested that the nitrogen atoms of the diamine should be bound to chiral centres (centers of asymmetricity, p7, line 2). We have found surprisingly that the chirality need not reside in these carbon atoms but may suitably be present in other parts of the diamine molecule, e.g. within $R^5$, $R^6$, $R^7$ or $R^8$ or linking group A.

The diamine ligand (I) is chiral. Preferably $R^5$, $R^6$, $R^7$ or $R^8$ or linking group A are chosen such that the ligand may be homochiral, i.e. (R,R) or (S,S) or have one (R) and one (S) centre. Preferably the chiral diamine is homochiral.

Linking group A provides a link between the carbon atoms to which the amine groups —$NR^1R^2$ and —$NR^3R^4$ are bound and comprises one or two substituted or unsubstituted carbon atoms. Substituting groups may replace one or both hydrogen atoms on the carbon atoms. The substituting groups may comprise one or more alkyl (C1-C20), alkoxy (C1-C20) or amino ($NR_2$, where R=hydrogen or alkyl) groups. The substituting groups may form one or more ring structures, e.g. a 4 to 7-membered ring structures incorporating one or more carbon atoms making up the linking group. Thus linking group A may comprise one or two carbon atoms forming part of one or more aromatic ring structures.

In one embodiment, the diamine is of formula (II)

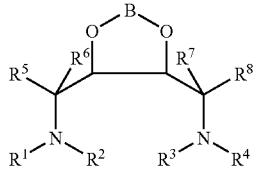

(II)

wherein $R^1$, $R^2$, $R^3$, $R^4$, $R^5$, $R^6$, $R^7$ and $R^8$ are as previously described and B is a linking group comprising one or two substituted or unsubstituted carbon atoms. Preferably $R^1$, $R^2$, $R^3$, $R^4$ are hydrogen, $R^5$, $R^6$, $R^7$ and $R^8$ are hydrogen or alkyl groups and B comprises $C(CH_3)_2$ or $(CH_3)(OCH_3)C$—$C(CH_3)(OCH_3)$.

In a further embodiment, the diamine is of formula (III)

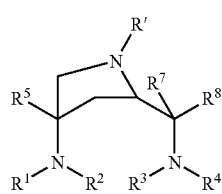

(III)

wherein $R^1$, $R^2$, $R^3$, $R^4$, $R^5$, $R^7$ and $R^8$ are as previously described and R' is a protecting group. Preferably $R^1$, $R^2$ and $R^5$ are hydrogen, $R^3$ and $R^4$ are hydrogen or alkyl, $R^7$ and $R^8$ are hydrogen, alkyl or aryl. It will be understood by persons skilled in the art that a wide range of protecting groups R' may be used for example alkyl, aryl, carboxylate, amido or sulphonate protecting groups may be used, e.g. benzyl ($CH_2C_6H_5$), methyl, tert-butyl, allyl, phenyl and substituted phenyls, $CO_2C(CH_3)_3$ (Boc), $CO_2CH_2C_6H_5$ (Cbz), ethyl carbonate, formamide, acetamides, benzamides, tosyl (Ts) and mesyl (Ms).

In a further embodiment, the diamine is of formula (IV)

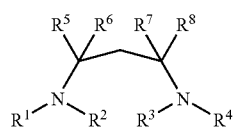

(IV)

wherein $R^1$, $R^2$, $R^3$, $R^4$, $R^5$, $R^6$, $R^7$ and $R^8$ are as previously described. Preferably $R^1$, $R^2$, $R^3$, $R^4$, $R^6$, $R^7$ are hydrogen and $R^5$ and $R^8$ are aryl or substituted aryl, most preferably $C_6H_5$.

In a further embodiment, the diamine has $R^1$, $R^2$, $R^3$, $R^4$ as hydrogen and is of formula (V)

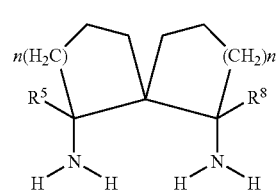

(V)

wherein $R^5$ and $R^8$ are as previously described and n=1 or 2. Preferably $R^5$ and $R^8$ are hydrogen.

Thus suitable chiral diamines include but are not restricted to the following;

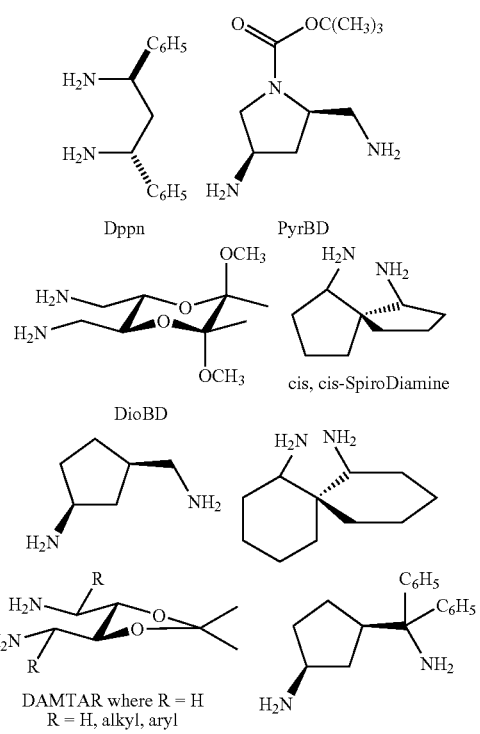

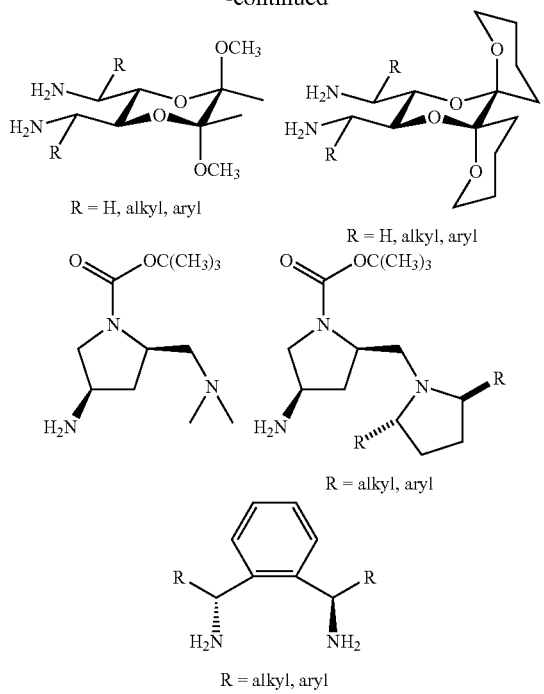

Particularly preferred diamines are PyrBD, DioBD, DAMTAR and dppn, more preferably PyrBD and DioBD, especially PyrBD.

We have found particularly effective combinations of bisphosphine, Group 8 metal and diamine of the present invention. Accordingly, group 8 transition metal catalysts of the present invention include but are not limited to the following;

where R=aryl, e.g. phenyl (Ph), tolyl (Tol) or xylyl (Xyl).

Particularly preferred catalysts are;

(i) (bisphosphine)RuCl$_2$-PyrBD catalysts where the bisphosphine is selected from the list comprising tol-BINAP and xyl-P-PHOS, (ii) (bisphosphine)RuCl$_2$-DioBD catalysts where the bisphosphine is selected from the list comprising tol-BINAP, and (iii) Xyl-P-PHOSRu(diamine) catalysts where the diamine is selected from the list consisting of dppn, PyrBd, DAMTAR and DioBD, particularly dppn.

These catalysts have been found to be more active and/or selective that their 1,2-diamine counterparts and other combinations of bisphosphine and diamine of the present invention.

The catalysts of the present invention may be readily prepared from the metal compound, phosphine and diamine. In general, the metal compound is combined with the phosphine in a suitable solvent and heated if necessary and then the diamine is added to form the desired metal complex catalyst. For example, P-PHOS compounds react under relatively mild conditions with [RuCl$_2$(benzene)$_2$]$_2$ and then 1,3-Dppn to form catalysts suitable for performing asymmetric hydrogenation reactions. This reaction is depicted below.

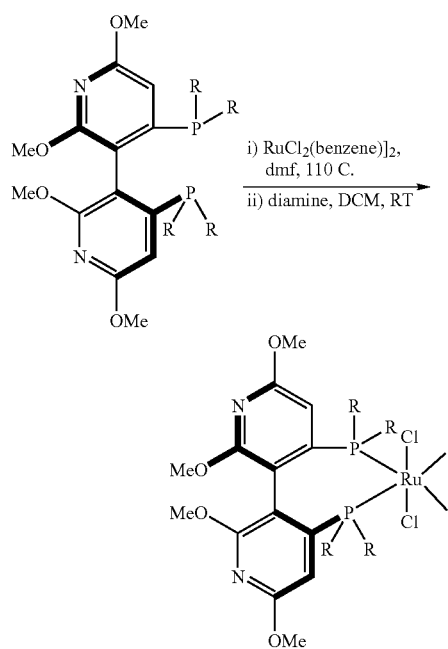

where R=aryl

The chiral metal complex catalysts of the present invention may be applied to a number of asymmetric reactions used to produce chiral products. Such reactions include but are not limited to the asymmetric hydrogenation of ketones and imines. To achieve high levels of enantiomeric purity in the reaction it is preferred that the metal complex comprises a substantially enantiomerically-pure phosphine and 1,3- or 1,4-diamine ligands of the present invention.

The conditions for using the metal complex catalysts are typically similar to those used for structurally related catalysts. For example, for the asymmetric reduction of ketones, the above catalyst may be used at room temperature under standard hydrogen pressures in combination with a strong base such as a sodium or potassium alkoxide, e.g. potassium tert-butoxide (KO$^t$Bu) to yield chiral alcohols in high yield and enantiomeric excess.

Ketones and imines that may be reduced using catalysts of the present invention may be of formula RCXR' in which R and R' are substituted or unsubstituted, saturated or unsaturated alkyl, cycloalkyl or aryl groups which may be linked and form part of a ring structure, e.g. a 5 or 6 membered ring structure, and X is O (Oxygen) or NR" in which R" may be alkyl, cycloalkyl or aryl which may be linked to R and/or R' as part of a ring structure.

We have found that the chiral catalysts of the present invention are able to catalyse the hydrogenation of alkyl- as well as aryl-ketones. Hydrogenation of alkyl-ketones, e.g. pinacolone, octanone, hexanone and cyclohexanone is extremely attractive and has not been successfully achieved with chiral bisphosphine ruthenium diamine catalysts heretofore. Thus a preferred use of the chiral catalysts of the present invention is the hydrogenation of alkyl ketones of formula RCOR' in which R and R' above are C1-C20 substituted or unsubstituted, saturated or unsaturated alkyl or cycloalkyl which may be linked and form part of a ring structure, e.g. a 5 or 6 membered ring structure.

The invention is further illustrated by reference to the following examples. Unless otherwise stated room temperature was 20-25° C.

EXAMPLE 1

Synthesis of Diphenyl-1,3-propanediamine (Dppn)

The diamine was prepared by the procedure of Roos et al. (Tetrahedron: Asymmetry 1999, 991-1000). The diol was prepared by transfer hydrogenation of the diketone by the procedure of Cossy (Tetrahedron Letters, 2001, 5005-5007).

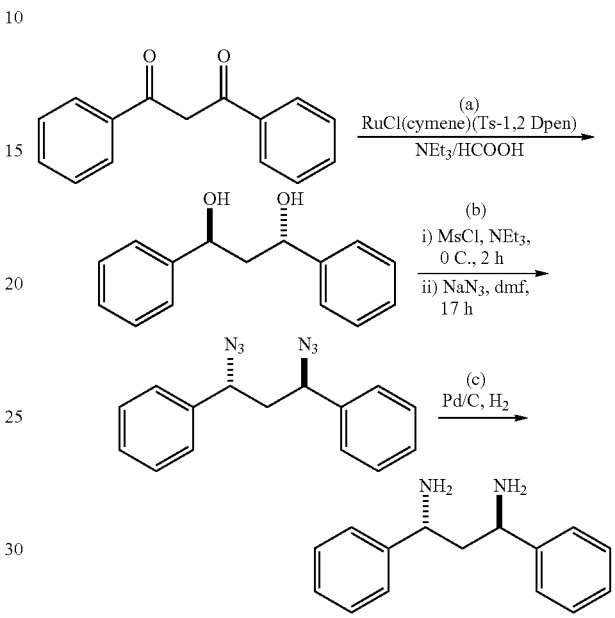

(a) 1,3-Diphenyl-1,3-Propanediol

A mixture of dibenzyloylmethane (2.5 g, 0.0117 mol), [RuCl(cymene)(R,R)Ts-Diphenylethylenediamine] (78 mg, 0.117 mmol) in triethylamine/formic acid azeotropic mix (5:2, 0.0234 mol) and dichloromethane (10 ml) was heated at 40° C. for 48 hrs. The solvent was removed in vacuo and the residue poured into water (100 ml) which resulted in the precipitation of a colourless solid. The solid was dried and used in the next step without further purification.

(b) 1,3-Diphenyl-1,3-Propanediazide

To the chiral 1,3-Diphenyl-1,3-Propanediol (0.150 g, 0.664 mmol) and triethylamine (0.205 g, 2.03 mmol) in tetrahydrofuran (THF) (5 ml) at 0° C. under nitrogen was added methanesulfonyl chloride (0.102 ml, 1.33 mmol). The mixture was allowed to warm to room temperature and stirred for 1 hr. The mixture was then filtered and the solid washed with a further portion of THF (5 ml). The solvent was then removed in vacuo to leave the crude product. To this crude product was added dimethylformamide (DMF) (2 ml) and sodium azide (0.135 g, 2.08 mmol) and the mixture stirred at room temperature overnight. Thin layer chromatography (TLC) indicated complete conversion of the starting material. The DMF was removed in vacuo and methyl-tert-butyl ether (MTBE) added (25 ml). The organic layer was washed with water (25 ml) and brine (25 ml). The solvent was removed to yield the diazide as a colourless solid.

$^1$H NMR (CDCl$_3$, 400 MHz) δ 7.7-7.0 (10H, m, Ar—H), 4.7 (2H, t, CH), 2.0 (2H, t, CH$_2$).

(c) 1,3-Diphenyl-1,3-Propanediamine (dppn)

A mixture of the diazide (0.1 g, 2.79 mmol) and Pd/C (10 wt % Pd, 0.010 g) was stirred in an autoclave under hydrogen gas (80 psi) for 2 hrs. The hydrogen was released and the mixture filtered through celite. The solvent was removed to give the diamine as initially a colourless solid which was recrystallised by using a minimum amount of chloroform.

$^1$H NMR (CDCl$_3$, 400 MHz) δ 7.7-7.0 (10H, m, Ar—H), 3.9 (2H, t, CH), 2.0 (2H, t, CH$_2$).

EXAMPLE 2

Preparation of Dppn-Catalysts a) Preparation of Ru[Cl$_2${(R/S)-Xyl-P-Phos}{(R,R)/(S,S)-DPPN}]

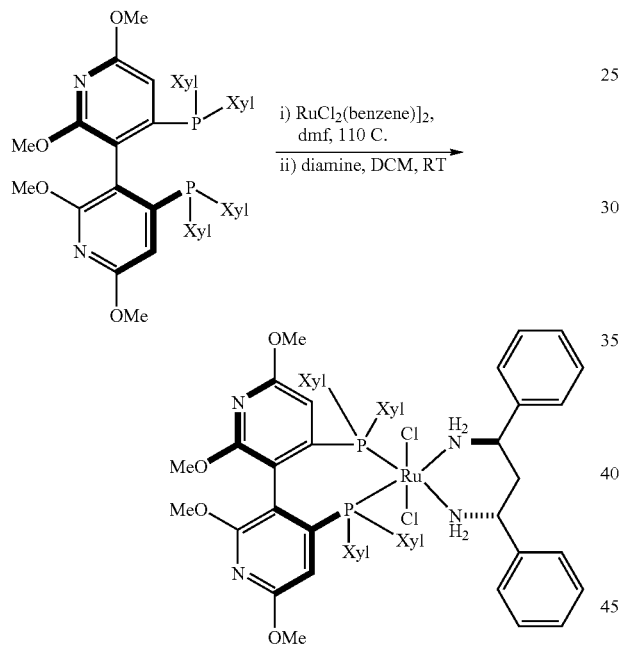

A solution of (R)- or (S)-Xyl-P-Phos (100 mg, 0.132 mmol) and [RuCl$_2$(benzene)] dimer (31.5 mg, 0.063 mmol) in Dimethylformamide (1 ml) was heated at 100 C for 2.5 hrs under N$_2$. The dark red reaction mixture was cooled to room temperature. To this crude complex was added a solution of the (R,R)- or (S,S)-Dppn diamine (0.138 mmol) in dichloromethane (1 ml) under nitrogen. The brown solution was stirred at room temperature overnight after which the solvent was removed in vacuo to yield the crude complex as a brown solid.

Trans-Ru[Cl$_2${(R)-Xyl-P-Phos}{(R,R)-DPPN}]. $^{31}$P NMR (400 MHz, CDCl$_3$) δ44.5 (s).

Trans-Ru[Cl$_2${(S)-Xyl-P-Phos}{(R,R)-DPPN}]. $^{31}$P NMR (400 MHz, CDCl$_3$) δ44.5 (s).

Trans-Ru[Cl$_2${(S)-Xyl-P-Phos}{(S,S)-DPPN}]. $^{31}$P NMR (400 MHz, CDCl$_3$) δ44.6 (s).

Trans-Ru[Cl$_2${(R)-Xyl-P-Phos}{(S,S)-DPPN}]. $^{31}$P NMR (400 MHz, CDCl$_3$) δ43.9 (s).

b) Preparation of Ru[Cl$_2${(R)-Xyl-BINAP}{(R,R)-DPPN}]

The above experiment was repeated combining (R)-Xyl-BINAP with [RuCl$_2$(benzene)] dimer and reacting this with the (R,R)-Dppn.

The crude product was obtained by removal of the solvent. Trans-Ru[Cl$_2${(R)-Xyl-BINAP}{(R,R)-DPPN}]. $^{31}$P NMR (400 MHz, CDCl$_3$) δ 45.3 (s).

EXAMPLE 3

Hydrogenation Reactions Using Dppn-Catalysts

General method: Asymmetric hydrogenation of ketones (substrate to catalyst S/c ratio 1000/1): 2-propanol (2 mL), ketone (2 mmol) and 0.1 M potassium tert-butoxide (KOtBu) (50 µL, 5×10$^{-3}$ mmol) were added in turn to a 25 mL autoclave charged with the ruthenium catalyst (2×10$^{-3}$ mmol), under inert atmosphere. The vessel was first purged with hydrogen three times and then pressurised with hydrogen to 8.3 bar. The reaction mixture was stirred at room temperature for the indicated time. The enantiomeric excess was determined by gas-chromatography using a Chirasil-DEX CB column.

Asymmetric hydrogenation of ketones (substrate to catalyst ratio=2500/1): 2-propanol (4.4 mL), ketone (5 mmol) and 0.1 M KOtBu (50 µL, 5×10$^{-3}$ mmol) were added in turn to a 25 mL autoclave charged with the ruthenium catalyst (2×10$^{-3}$ mmol), under inert atmosphere. The vessel was first purged with hydrogen three times and then pressurized with hydrogen to 145 psi. The reaction mixture was stirred at room temperature for the indicated time. The enantiomeric excess was determined by gas-chromatography using a Chirasil-DEX CB column.

a) Hydrogenation of Acetophenone

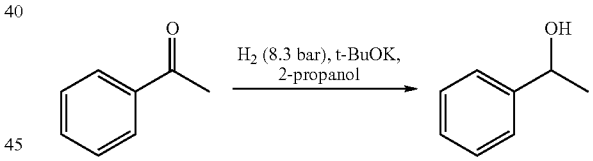

Using the general method, the Dppn-catalysts of Example 2 gave the following results;

| Catalyst | S/c | Time (hrs) | Conv. (%) | Ee (%) |
|---|---|---|---|---|
| (R)Xyl-P-Phos-RuCl$_2$-(R,R)-Dppn | 1000 | 3 | 100 | 93 |
| (R)Xyl-P-Phos-RuCl$_2$-(R,R)-Dppn | 2500 | 3 | 100 | 95 |
| (R)Xyl-P-Phos-RuCl$_2$-(R,R)-Dppn | 2500 | 2.5 | 100 | 95 |
| (R)Xyl-P-Phos-RuCl$_2$-(R,R)-Dppn | 2500 | 6.5 | 95 | 95 |
| (S)Xyl-P-Phos-RuCl$_2$-(R,R)-Dppn | 1000 | 5 | 100 | 69 |
| (S)Xyl-P-Phos-RuCl$_2$-(R,R)-Dppn | 2500 | 6 | 100 | 74 |
| (R)Xyl-P-Phos-RuCl$_2$-(R,R)-Dppn | 1000# | 12 | 100 | 95 |
| (S)Xyl-P-Phos-RuCl$_2$-(S,S)-Dppn | 2500# | 12 | 100 | 95 |
| (S)Xyl-P-Phos-RuCl$_2$-(S,S)-Dppn | 10000* | 24 | 100 | 95.3 |

Hydrogenated at 10bar
*General method as for S/c 2500/1

In comparison to Xyl-P-Phos, when unsubstituted (R)-P-Phos was used as the chiral bisphosphine in combination with (R,R)-Dppn, the ruthenium catalyst was less selective and after a reaction time of 18 hours gave a lower ee of 36%. This result shows the particular effectiveness of the combination of xyl-P-Phos and dppn in the Ru catalysed hydrogenation of aryl ketones.

b) Hydrogenation of Substituted Acetophenones

Using the general methods described in Example 3, hydrogenation was performed at 10 bar hydrogen on 2-propanol solutions of substituted acetophenones using (R)Xyl-P-Phos-RuCl$_2$-(R,R)-Dppn or (S)Xyl-P-Phos-RuCl$_2$-(S,S)-Dppn. The base/catalyst ratio was 50/1 for all. The results are given below;

| Ketone | Catalyst | S/c | Time (h) | Conv. (%) | Ee (%) |
|---|---|---|---|---|---|
| R = p-F | (S, SS) | 2500 | 14 | >99 | 95 |
| R = p-OMe | (S, SS) | 2500 | 14 | >99 | 97.3 |
| R = m-Me | (S, SS) | 2500 | 12 | >99 | 96.4 |
| R = o-Me | (R, RR) | 1000 | 20 | >99 | 86 |
| R = o-OMe | (R, RR) | 1000 | 24 | >99 | 84 |
| R = bis 3,5-CF$_3$ | (S, SS) | 1000 | 10 | >99 | 95.7 |

The results show the catalysts to give good selectivities irrespective of the presence of electron donating or withdrawing substituents on the para or meta positions.

c) Hydrogenation of Pinacolone

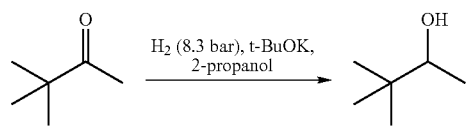

Using the general method with the Dppn-catalysts of Example 2 gave the following results;

| Catalyst | S/c | Time (hrs) | Conv (%). | Ee (%) |
|---|---|---|---|---|
| (R)Xyl-P-Phos-RuCl$_2$-(R,R)-Dppn | 1000 | 16 | 46 | 65 |
| (R)Xyl-BINAP-RuCl$_2$-(R,R)-Dppn | 1000 | 16 | 48 | 60 |

A comparative experiment was performed using the general method with a comparative 1,2-diamine catalyst based on 1,2-diphenylethylenediamine (Dpen).

| Comparative Catalyst | S/c | Time (hrs) | Conv (%). | Ee (%) |
|---|---|---|---|---|
| (R)Xyl-BINAP-RuCl$_2$-(R,R)-Dpen | 1000 | 16 | 30 | 11 |

The results demonstrate that the Dppn-catalysts of Example 2 can give an improved yield and enantiomeric excess over the comparative 1,2-diamine catalyst.

EXAMPLE 4

Synthesis of (3-Aminomethyl-5-6-dimethoxy-5-6-Dimethyl[1,4]-dioxan-2-yl]-methylamine [(S,S)-DioBD]

The intermediate diol was prepared according to literature procedure for steps (a) and (b). (Ley, J. Chem. Soc., Perkin Trans 1, 1999, 1627).

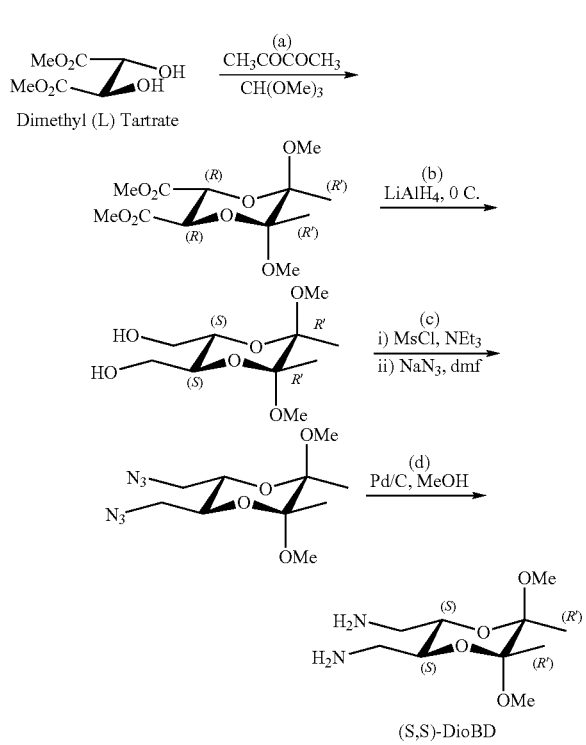

(a) (3-hydroxymethyl-5-6-dimethoxy-5-6-Dimethyl [1,4]dioxan-2-yl]methylalcohol

A mixture of dimethyl-(L)-tartrate (4.578 g, 0.0257 mol), 2,3-butadione (2.65 g, 0.0308 mol), trimethyl orthoformate (11.41 g, 0.0771 mol) and camphor sulphonic acid (0.597 g, 2.57 mmol) in anhydrous methanol was refluxed overnight (17 hrs) under nitrogen. The reaction was cooled and the solvent removed by rotary evaporation to give the crude product as a brown solid. The material was passed through a column of silica to give the pure product.

(b) To a Solution of the Diester (3.2 g, 0.011 mol) in Dry THF at 0° C. was Added a Solution of LiAlH$_4$ (1M, 11 ml, 0.011 mol) dropwise. After the addition was complete the reaction mixture was allowed to warm to room temperature and stirred for 1 hr. The reaction was then cooled to 0° C. and ethylacetate (EtOAc) (5 ml) was added. The reaction mixture was then poured into saturated aqueous ammonium chloride solution and extracted with EtOAc (3×100 ml). The solvent was removed to give the crude diol as a light brown solid, which was used without any further purification.

(c) (3-azidomethyl-5-6-dimethoxy-5-6-dimethyl[1,4]dioxan-2-yl]methylazide

To a solution of the diol (1.816 g, 7.69 mmol) and triethylamine (4.28 ml, 0.03 mmol) in dry THF (15 ml) at 0° C. under $N_2$ was added dropwise methansulphonyl chloride (1.25 ml, 0.016 mol). The reaction mixture was allowed to warm to room temperature and the stirred for 1 h. The mixture was then filtered and the solid washed with THF (2×5 ml). The THF was removed in vacuo to give the crude product. To this crude product was added sodium azide (1.08 g, 0.0169 mol) and DMF (5 ml). The mixture was heated at 60° C. for 14 hrs. Then the DMF was removed under high vacuum. MTBE was then added and the organic phase washed with water (3×100 ml) and brine, dried over anhydrous $MgSO_4$ and the solvent removed to give the crude product. The diazide was obtained by column chromatography eluting with hexane-EtOAc (9:1) to give the product as a white solid (0.8 g).

$^1$H NMR ($CDCl_3$, 400 MHz) δ 3.8 (1H, t, J 2.5, 3.3 (1H, m, CHH), 3.25 (3H, s, $OCH_3$), 3.15 (1H, dd, J 13 and 2.5, CHH), 1.25 (3H, s, $CH_3$); $^{13}$C NMR ($CDCl_3$, 100 MHz) 100 (C), 69 (CH), 50.8 ($CH_3$), 48.1 ($CH_2$), 17.3 ($CH_3$).

(d) (3-Aminomethyl-5-6-dimethoxy-5-6-Dimethyl[1,4]dioxan-2-yl]methylamine [(S,S)DioBD]

A mixture of the diazide (0.8 g, 2.79 mmol) and Pd/C (10 wt % Pd, 0.025 g) was stirred in an autoclave under $H_2$ (80 psi) for 2 hrs. The $H_2$ was released and the mixture filtered through celite.

The solvent was removed to give the diamine as initial a colourless oil which eventually solidified upon standing.

$^1$H NMR ($CDCl_3$, 400 MHz) δ 3.52 (1H, m, CH), 3.2 (3H, s, $OCH_3$), 2.7 (2H, br d, J 4, $CH_2$), 1.25 (3H, s, $CH_3$); $^{13}$C NMR ($CDCl_3$, 100 MHz) δ 98.5 (C), 71.1 (CH), 47.9 ($CH_3$), 42.6 ($CH_2$), 17.6 ($CH_3$).

EXAMPLE 5

Preparation of DioBD Catalysts (a) Preparation of Ru[$Cl_2${(R/S)-Tol-BINAP}{(S,S)-DioBD}]

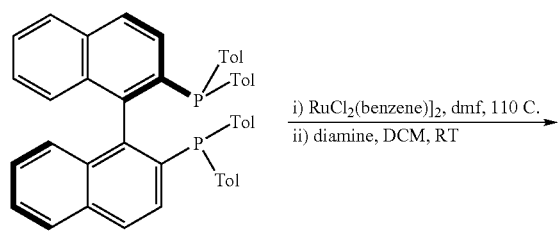

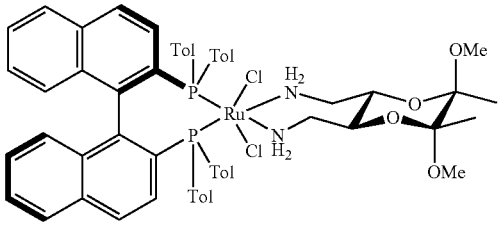

A solution of (R)- or (S)-TolBinap (100 mg, 0.147 mmol) and [$RuCl_2$(benzene)] dimer (37 mg, 0.0737 mmol) in Dimethylformamide (1 ml) was heated at 110° C. for 15 mins under $N_2$. The dark red reaction mixture was cooled and the DMF removed in vacuo. To this crude complex was added a solution of the (S,S)-DioBD diamine (34 mg, 0.147 mmol) in dichloromethane (5 ml) under nitrogen. The yellowish solution was stirred at room temperature for 1 hr after which the solvent was removed in vacuo. The complex was extracted from the crude solid by addition of hexane: MTBE (1:1, 10 ml), filtration and removal of the solvent which resulted in the precipitation of a yellow solid. The solvent was completely removed and to give the complex as a yellow solid.

Ru[$Cl_2${(S)-Tol-BINAP}{(S,S)-DiOBD}]: $^{31}$P NMR ($CDCl_3$, 400 MHz) δ 44.8

Ru[$Cl_2${(R)-Tol-BINAP}{(S,S)-DiOBD}]: $^{31}$P NMR ($CDCl_3$, 400 MHz) δ 45.4

EXAMPLE 6

Hydrogenation Reactions using DioBD-Catalysts (a) Hydrogenation of Tetralone

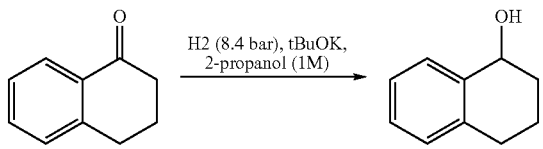

2-propanol (1 mL), tetralone (1 mmol) and 0.1 M KOtBu (50 μL, 5×10$^{-3}$ mmol) were added in turn to a 25 mL autoclave charged with the ruthenium catalyst (2×10$^{-3}$ mmol), under inert atmosphere. The vessel was first purged with hydrogen three times and then pressurized with hydrogen to 8.3 bar. The reaction mixture was stirred at room temperature for the indicated time. The enantiomeric excess was determined by GC using a Chirasil-DEX CB column. Using this method, the DioBD-catalyst of Example 5 gave the following results;

| Catalyst | S/c | Time (hrs) | Conv. (%) | Ee (%) |
|---|---|---|---|---|
| (S)TolBINAP-RuCl$_2$-(S,S)-DioBD | 500 | 16 | 23.5 | 81 |

A comparative experiment was performed using the same method with a comparative 1,2-diamine catalyst based on 1,2-diphenylethylenediamine (Dpen).

| Comparative Catalyst | S/c | Time (hrs) | Conv. | Ee (%) |
|---|---|---|---|---|
| (S)TolBINAP-RuCl$_2$-(S,S)-Dpen | 500 | 16 | 98 | 24 |

The result demonstrates that the DioBD-catalysts of Example 5 can give an improved enantiomeric excess over the comparative 1,2-diamine catalyst.

EXAMPLE 7

Synthesis of (2S,4S)-4-Amino-2-aminomethylpyrrolidine-1-carboxylic acid tert-butyl ester (PyrBD)

The synthesis is based on the commercially available trans diol. Ganesh (Organic Letters, 2001, 3, 103), has reported the synthesis of these diamines for use as analogues that stabilise DNA duplexes and triplexes.

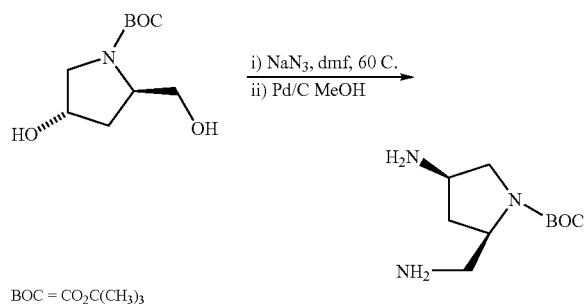

BOC = CO$_2$C(CH$_3$)$_3$ (2S,4R)-4-Methanesulfonyloxy-2-methanesulfonyloxymethylpyrrolidine-1-carboxylic acid tert-butyl ester: To a solution of alcohol (~15 mmol) and triethylamine (6.5 mL, 45 mmol) in THF (100 mL) was slowly added mesylchloride (MsCl) (2.6 mL, 33 mmol). After stirring for 30 min at room temperature, the precipitated salts were filtered off and the reaction mixture was treated with saturated aqueous NH$_4$Cl (100 mL). The aqueous phase was extracted with MTBE (2×75 mL). The combined organic layers were washed with saturated aqueous NaHCO$_3$ (100 mL) and brine (100 mL), dried over anhydrous MgSO$_4$ and concentrated under reduced pressure to afford 4.67 g (12.5 mmol, 83%) of a white solid which was used without further purification.

(i) (2S,4S)-4-Azido-2-azidomethylpyrrolidine-1-carboxylic acid tert-butyl ester: A solution of mesylate (4.67 g, 12.5 mmol) and NaN$_3$ (2.43 g, 37.5 mmol) in DMF (50 mL) was heated at 90° C. for 24 hrs. After cooling down to room temperature, the reaction mixture was diluted with MTBE (50 mL) and washed with H$_2$O (5×50 mL). The organic phase was then dried (anhydrous MgSO$_4$) and concentrated under reduced pressure to afford a solid which was used without further purification. $^1$H NMR (CDCl$_3$, 400 MHz) δ 4.1 (1H, br s), 3.9 (1H, br m), 3.65 (1H, br s), 3.5-3.2 (3H, br m), 2.2 (1H, m), 2.0 (1H, m), 1.4 (9H, s).

(ii) (2S,4S)-4-Amino-2-aminomethylpyrrolidine-1-carboxylic acid tert-butyl ester. A mixture of the diazide (0.8 g, 2.79 mmol) and Pd/C (10 wt % Pd, 0.025 g) was stirred in an autoclave under hydrogen (80 psi) for 2 hrs. The hydrogen pressure was released and the mixture filtered through celite. The solvent was removed to give the diamine as a colourless oil.

$^1$H NMR (CDCl$_3$, 400 MHz) δ 3.75 (2H, br s), 3.4 (1H, m), 3.0-2.7 (3H, m), 2.25 (1H, m), 1.5-1.3 (10H, m).

EXAMPLE 8

Preparation of PyrBD Catalysts a) Preparation of Ru[Cl$_2${(R/S)-Tol-BINAP}{(S,S)-PyrBD}]

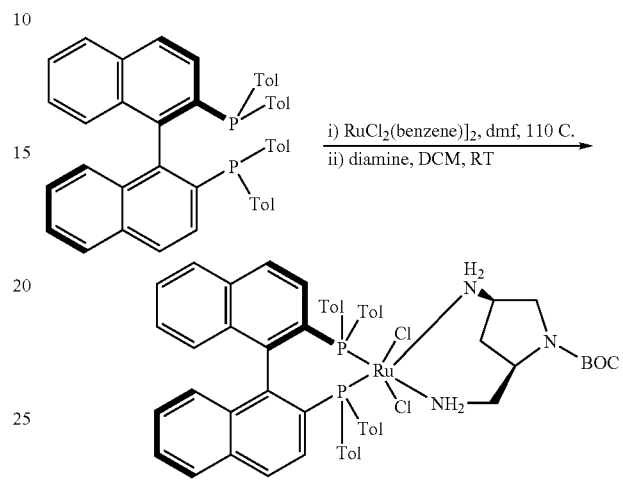

A solution of (R)- or (S)-Tol-Binap (100 mg, 0.147 mmol) and [RuCl$_2$(benzene)] dimer (37 mg, 0.0737 mmol) in Dimethylformamide (1 ml) was heated at 105° C. for 15 mins under nitrogen. The dark red reaction mixture was cooled and the DMF removed in vacuo. To this crude complex was added a solution of the (S,S)-PyrBD diamine (34 mg, 0.147 mmol) in dichloromethane (5 ml) under nitrogen. The yellowish solution was stirred at room temperature for 1 hr after which the solvent was removed in vacuo. The complex was extracted from the crude solid by addition of hexane:MTBE (1:1, 10 ml), followed by filtration and removal of the solvent which resulted in the precipitation of a yellow solid. The solvent was removed under vacuo to give the complex as a yellow solid.

Ru[Cl$_2${(R)-Tol-BINAP}{(S,S)-PyrBD}]: $^{31}$P NMR (CDCl$_3$, 400 MHz) δ 45.2 (d, J 37) and δ 41.3 (d, J 37)

Ru[Cl$_2${(S)-Tol-BINAP}{(S,S)-PyrBD}]: $^{31}$P NMR (CDCl$_3$, 400 MHz) δ 44.5 (d, J 37) and δ 42.3 (d, J 37)

b) Preparation of Ru[Cl$_2${(R/S)-Xyl-P-Phos}{(S,S)-PyrBD}]

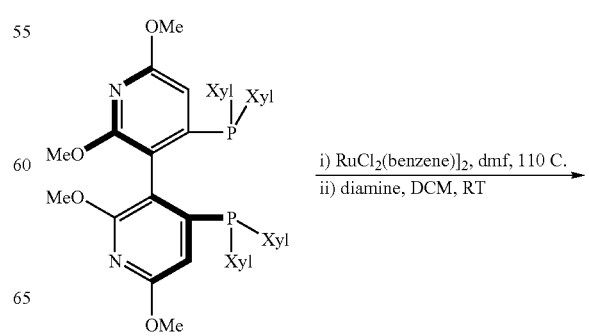

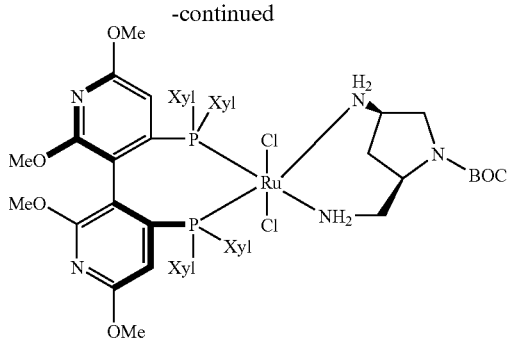

A solution of (R)- or (S)-Xyl-P-Phos (51 mg, 0.066 mmol) and [RuCl₂(benzene)] dimer (16.8 mg, 0.0315 mmol) in Dimethylformamide (1 ml) was heated at 100° C. for 2.5 hrs under nitrogen. The dark red reaction mixture was cooled to room temperature. To this crude complex was added a solution of the (S,S)-PyrBD diamine (0.067 mmol) in dichloromethane (1 ml) under nitrogen. The brown solution was stirred at room temperature overnight after which the solvent was removed in vacuo to yield the crude complex as a brown solid.
Ru[Cl₂{(R)-Xyl-P-Phos}{(S,S)-PyrBD}]: $^{31}$P NMR (CDCl₃, 400 MHz) δ 45.2 (d, J 37) and δ 41.3 (d, J 30)
Ru[Cl₂{(S)-Xyl-P-Phos}{(S,S)-PyrBD}]: $^{31}$P NMR (CDCl₃, 400 MHz) δ 44.6 (d, J 37) and δ 41.7 (d, J 37)

EXAMPLE 9

Hydrogenation Reactions Using PyrBD-Catalysts a) Hydrogenation of (3'5')-bis(trifluoromethyl)acetophenone

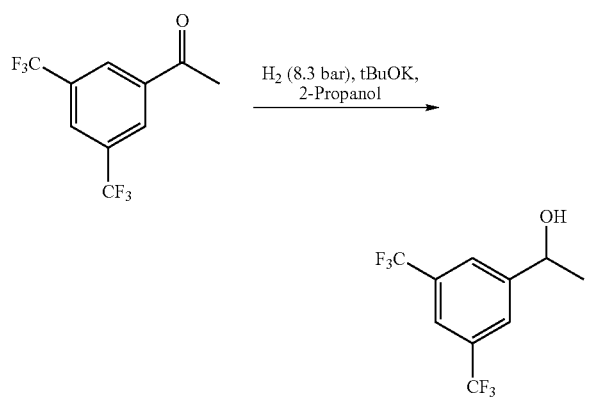

Hydrogenation was performed according to the general method described in Example 3. The PyrBD-catalysts of Example 8 gave the following results;

| Catalyst | S/c | Time (hrs) | Conv. (%) | Ee (%) |
|---|---|---|---|---|
| (S)Xyl-P-Phos-RuCl₂-PyrBD | 1000 | 16 | >98 | 69 |
| (R)Xyl-P-Phos-RuCl₂-PyrBD | 1000 | 16 | >98 | 91 |

A comparative experiment was performed using the general method with a comparative 1,2-diamine catalyst based on 1,2-diphenylethylenediamine (Dpen).

| Comparative Catalyst | S/c | Time (hrs) | Conv. | Ee (%) |
|---|---|---|---|---|
| (R)Xyl-P-Phos-RuCl2-(R,R)Dpen | 1000 | 16 | >98 | 60 |

The result demonstrates that the PyrBD-catalysts of Example 8 can give an improved enantiomeric excess over the comparative 1,2-diamine catalyst.

b) Hydrogenation of Isobutyrophenone

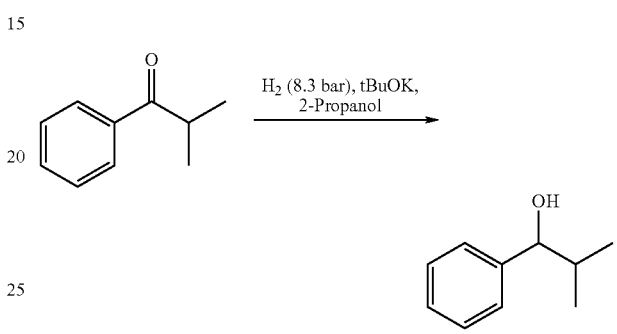

Hydrogenation was performed according to the general method described in Example 3. The PyrBD-catalyst of Example 8 gave the following results;

| Catalyst | S/c | Time (hrs) | Conv. (%) | Ee (%) |
|---|---|---|---|---|
| (S)TolBINAP-RuCl₂-(S,S)PyrBD | 1000 | 14 | >98 | 80 |

A comparative experiment was performed using the general method with a comparative 1,2-diamine catalyst based on 1,2-diphenylethylenediamine (Dpen).

| Comparative Catalyst | S/c | Time (hrs) | Conv. | Ee (%) |
|---|---|---|---|---|
| (S)TolBINAP-RuCl₂-(S,S)Dpen | 1000 | 48 | 81 | 87 |

The result demonstrates that the PyrBD-catalysts of Example 8 can give an improved activity and yield with comparable enantiomeric excess with the comparative 1,2-diamine catalyst.

EXAMPLE 10

Preparation of (2S,3S)-2,3-O-isopropylidenebutane 1,4 diamine, DAMTAR

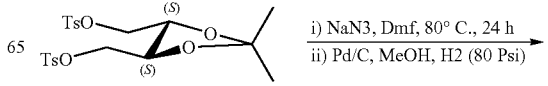

-continued

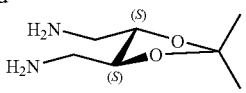

A mixture of (S,S),(−) 1,4-Di-O-p-toluolsulphonyl-2,3-O-isopropylidene-L-threitol (1.88 g, 4 mmol) and NaN3 (0.63 g, 10 mmol) in dmf (10 ml) was heated at 80° C. for 24 hrs. The dmf was removed in vacuo and the residue suspended in MTBE (150 ml). The organic layer was washed with water (3×100 ml), brine (100 ml), dried over MgSO4, filtered and the solvent removed by rotary evaporation to give the crude diazide. The product was obtained by column chromatography on silica gel, eluting with hexane:EtOAC (9:1) to give the pure diazide as a colourless liquid.

$^1$H NMR (CDCl$_3$, 400 MHz) δ 3.90 (1H, CH), 3.30 (2H, dddd, CH$_2$), 1.3 (3H, s, CH$_3$); $^{13}$C NMR (CDCl$_3$, 100 MHz) δ 110 (C), 76.6 (CH), 51.6 (CH$_2$), 26.8 (CH$_3$).

[(S,S) DAMTAR]

A mixture of the diazide (0.8 g, 2.79 mmol) and Pd/C (10 wt % Pd, 0.025 g) was stirred in an autoclave under H$_2$ (80 psi) for 2 hrs. The H$_2$ was released and the mixture filtered through celite. The solvent was removed to give the diamine as a colourless oil which eventually solidified upon standing.

$^1$H NMR (CDCl$_3$, 400 MHz) δ 3.7 (1H, CH), 2.7 (2H, m, CH$_2$), 1.25 (3H, s, CH$_3$).

EXAMPLE 11

Preparation of DAMTAR Catalysts (a) Preparation of Ru[Cl$_2${(R/S)-Tol-BINAP}{(R,R/S,S)-DAMTAR}]

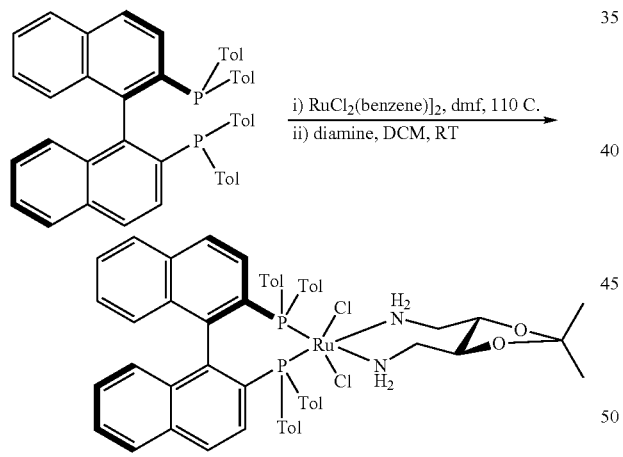

A solution of (R)- or (S)-Tol-Binap (100 mg, 0.147 mmol) and [RuCl$_2$(benzene)] dimer (37 mg, 0.0737 mmol) in Dimethylformamide (1 ml) was heated at 110° C. for 15 mins under N$_2$. The dark red reaction mixture was cooled and the dmf removed in vacuo. To this crude complex was added a solution of the (S,S)-DAMTAR diamine (34 mg, 0.147 mmol) in dichloromethane (5 ml) under nitrogen. The yellow solution was stirred at room temperature for 1 hr after which the solvent was removed in vacuo. The complex was extracted from the crude solid by addition of hexane:MTBE (1:1, 10 ml), filtration and removal of the solvent which resulted in the precipitation of a yellow solid. The solvent was completely removed and to give the complex as a yellow solid.

(Ru[Cl$_2${(R)-Tol-Binap}{(R,R)-DAMTAR}]. $^{31}$P NMR (400 MHz, CDCl$_3$) δ45.5 (s).

Ru[Cl$_2${(R)-Tol-Binap}{(S,S)-DAMTAR}]. $^{31}$P NMR (400 MHz, CDCl$_3$) δ44.8 (s).

The method was repeated using (S)-BINAP and (R)- and (S)-Xyl-BINAP. The analyses of the resulting products were as follows;

Ru[Cl$_2${(S)-Binap)}{(R,R-DAMTAR}]. $^{31}$P NMR (400 MHz, CDCl$_3$) δ46.3 (s).

Ru[Cl$_2${(R)-Xyl-Binap}{(R,R)-DAMTAR}]. $^{31}$P NMR (400 MHz, CDCl$_3$) δ45 (s).

Ru[Cl$_2${(S)-Xyl-Binap}{(R,R)-DAMTAR}]. $^{31}$P NMR (400 MHz, CDCl$_3$) δ45.2 (s).

Ru[Cl$_2${(R)-Xyl-Binap}{(S,S)-DAMTAR}]. $^{31}$P NMR (400 MHz, CDCl$_3$) δ45.2 (s).

(b) Preparation of Ru[Cl$_2${(R/S)-Xyl-P-PHOS}{(R,R/S,S)-DAMTAR}]

A solution of (R)- or (S)-Xyl-P-PHOS (100 mg, 0.132 mmol) and [RuCl$_2$(benzene)] dimer (31.5 mg, 0.063 mmol) in Dimethylformamide (1 ml) was heated at 100° C. for 2.5 hrs under N$_2$. The dark red reaction mixture was cooled to room temperature. To this crude complex was added a solution of the (R,R)- or (S,S)-DAMTAR diamine (0.138 mmol) in dichloromethane (1 ml) under nitrogen. The brown solution was stirred at room temperature overnight after which the solvent was removed in vacuo to yield the crude complex as a brown solid.

Ru[Cl$_2${(R)-Xyl-P-PHOS}{Cl$_2$(R,R)-DAMTAR}]. $^{31}$P NMR (400 MHz, CDCl$_3$) δ443.7 (s).

Ru[Cl$_2${(S)-Xyl-P-PHOS}{$_2$(R,R)-DAMTAR}]. $^{31}$P NMR (400 MHz, CDCl$_3$) δ43.4 (s).

Ru[Cl$_2${(S)-Xyl-P-PHOS}{$_2$(S,S)-DAMTAR}]. $^{31}$P NMR (400 MHz, CDCl$_3$) δ43.7 (s).

The method was repeated using (R)- and (S)-P-PHOS. The analyses of the resulting products were as follows;

Ru[Cl$_2${(R)-P-PHOS}{(R,R)-DAMTAR}]. $^{31}$P NMR (400 MHz, CDCl$_3$) δ45.4 (s).

Ru[Cl$_2${(R)-P-PHOS}{Cl$_2$(S,S)-DAMTAR}]. $^{31}$P NMR (400 MHz, CDCl$_3$) δ44.6 (s).

Ru[Cl$_2${(S)-P-PHOS}{Cl$_2$(R,R)-DAMTAR}]. $^{31}$P NMR (400 MHz, CDCl$_3$) δ44.8 (s).

Ru[Cl$_2${(S)-P-PHOS}{$_2$(S,S)-DAMTAR}]. $^{31}$P NMR (400 MHz, CDCl$_3$) δ45.4 (s).

EXAMPLE 12

Hydrogenation Reactions Using DAMTAR Catalysts a) Hydrogenation of isopropyl-phenyl ketone

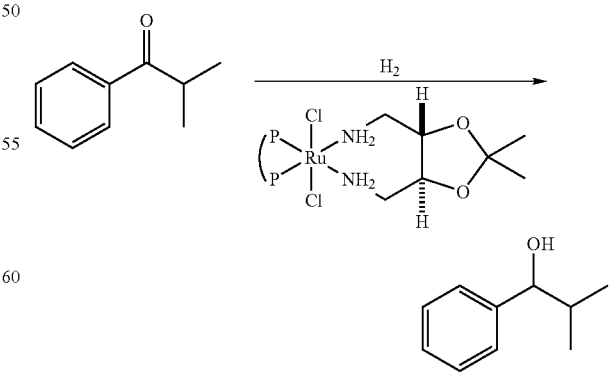

The general hydrogenation procedure of Example 3 was followed. For comparison, a series of 1,2-diamine catalysts were also tested. The results are given below;

| Catalyst | S/C | Time (hrs) | Alcohol Config. | Conv. (%) | Ee (%) |
| --- | --- | --- | --- | --- | --- |
| ((R)-P-Phos)RuCl$_2$(R,R-DAMtar) | 1000/1 | 3 | R | 100 | 95 |
| ((R)-P-Phos)RuCl$_2$(S,S-DAMtar) | 1000/1 | 2.5 | R | 100 | 92 |
| ((S)-P-Phos)RuCl$_2$(R,R-DAMtar) | 1000/1 | 2 | S | 100 | 97 |
| ((S)-P-Phos)RuCl$_2$(S,S-DAMtar) | 1000/1 | 5 | S | 100 | 95 |
| ((S)-P-Phos)RuCl$_2$(R,R-DAMtar) | 1000/1 | 2.5 | S | 100 | 93 |
| ((S)-P-Phos)RuCl$_2$(R,R/S,S-DAMtar) | 1000/1 | 3 | S | 100 | 96 |
| ((R)-P-Phos)RuCl$_2$(R,R/S,S-DAMtar) | 1000/1 | 3 | R | 100 | 90-92 |
| ((S/R-P-Phos)RuCl$_2$(S,S-DAMtar) | 1000/1 | 2 | — | 100 | 9 |
| ((R)-Xyl-P-Phos)RuCl$_2$(R,R-DAMtar) | 1000/1 | 20 | R | 100 | 46 |
| ((S)-Xyl-P-Phos)RuCl$_2$(R,R-DAMtar) | 1000/1 | 6 | S | 100 | 75 |
| ((R)-Tol-Binap)RuCl$_2$(R,R-DAMtar) | 1000/1 | 5 | R | 100 | 90 |
| ((R)-Tol-Binap)RuCl$_2$ (S,S-DAMtar) | 1000/1 | 2 | R | 100 | 90 |
| ((S)-Tol-Binap)RuCl$_2$(S,S-DAMtar) | 1000/1 | 6 | S | 100 | 94 |
| ((S)-Tol-Binap)RuCl$_2$(S,S/R,R-DAMtar) | 1000/1 | 2 | S | 100 | 96 |
| ((S)-Tol-Binap)RuCl$_2$(R,R-DAMtar) | 1000/1 | 2 | S | 100 | 97 |
| ((S)-Tol-Binap)RuCl$_2$(R,R-DAMtar) | 1000/1 | 2.5 | S | 100 | 97 |
| ((S)-Binap)RuCl$_2$(R,R-DAMtar) | 1000/1 | 3.5 | S | 37 | 96 |
| ((R)-Xyl-Binap)RuCl$_2$(R,R-DAMtar) | 1000/1 | 17 | R | 100 | 68 |
| ((S)-Xyl-Binap)RuCl$_2$(R,R-DAMtar) | 1000/1 | 14 | S | 100 | 58 |
| Comparative Examples | | | | | |
| ((S)-Tol-Binap)RuCl$_2$(S,S-DPEN) | 1000/1 | 3.5 | R | 50 | 73 |
| ((S)-P-Phos)RuCl$_2$(S,S-DPEN) | 1000/1 | 3.5 | — | — | — |
| ((S)-Xyl-P-Phos)RuCl$_2$(S,S-DPEN) | 1000/1 | 3.5 | — | 1 | — |
| ((S)-PhanePhos)RuCl$_2$(R,R-DPEN) | 1000/1 | 3.5 | S | 75 | 68 |
| ((S)-Xyl-PhanePhos)RuCl$_2$(R,R-DPEN) | 1000/1 | 3.5 | R | 19 | 8 |

The results show that excellent selectivities can be obtained using the combination of a phosphine and DAMTAR. Without wishing to be bound by theory it appears that the phosphine may be influencing the selectivity more so that a chiral phosphine in the presence of the racemic diamine can give high ee.

b) Hydrogenation of Tetralone

Using the general method of example 3 tetralone was hydrogenated with a range of DAMTAR catalysts. The results are given below;

| Catalyst | S/C | Time (hrs), Temp. | Alcohol Config. | Conv. (%) | Ee (%) |
| --- | --- | --- | --- | --- | --- |
| (S)-P-Phos)RuCl$_2$(S,S-DAMtar) | 250 | 20, 30° C. | R | 99 | 88 |
| ((S)-Xyl-P-Phos)RuCl$_2$(R,R-DAMtar) | 500 | 20, 40° C. | R | 27 | 96 |
| ((S)-Xyl-P-Phos)RuCl$_2$(R,R-DAMtar) | 250 | 0.6, 40° C. | R | 99 | 96 |
| ((R)-Tol-Binap)RuCl$_2$(R,R-DAMtar) | 250 | 48, 30° C. | S | 98 | 79 |
| ((S)-Binap)RuCl$_2$(R,R-DAMtar) | 500 | 20, 40° C. | R | 28 | 86 |
| ((R)-Xyl-Binap)RuCl$_2$(S,S-DAMtar) | 500 | 20, 40° C. | S | 55 | 96 |
| ((S)-Xyl-Binap)RuCl$_2$(S,S-DAMtar) | 500 | 20, 40° C. | S | 8 | 87 | c) Hydrogenation of Substituted Tetralones

Using the general method of Example 3 a series of substituted tetralones were hydrogenated. The results are given below;

| Ketone | Catalyst | Time (hrs) | conv (%) | Ee (%) |
|---|---|---|---|---|
| MeO-tetralone (7-MeO) | ((S)Xyl-P-Phos)RuCl$_2$(R,R)-DAMtar | 0.15 | 96 | 91 |
| MeO-tetralone (6-MeO) | ((S)Xyl-P-Phos)RuCl$_2$(R,R)-DAMtar | 0.4 | 98 | 98 |
| 2-methyl tetralone | ((S)P-Phos)-RuCl$_2$(R,R)-DAMTar | 2 | 99 | ≧90 (98:2 syn:anti) |

The results show that excellent ee's may be obtained using DAMTAR.

EXAMPLE 13

Preparation of cis,cis-SpiroDiamine

The trans,trans SpiroDiol intermediate was prepared according to literature procedure report by Chan (*Tetrahedron Letters*, 2000, 4425).

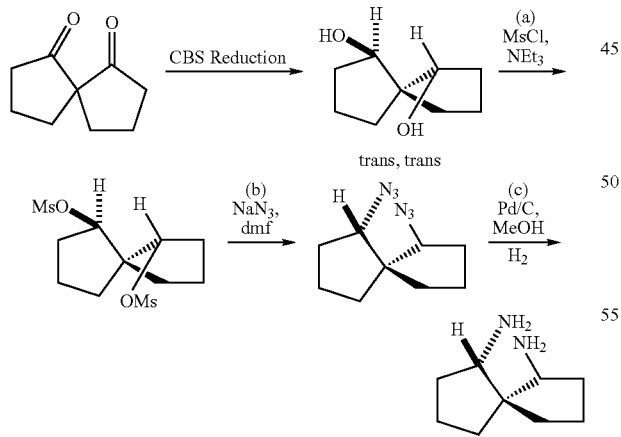

(a) Cis, Cis Spiro-mesylate: To a solution of trans, trans diol (0.27 g, 1.74 mmol) and triethylamine (0.97 ml, 6.97 mmol) in THF (5 mL) was slowly added mesyl chloride (MsCl) (0.29 ml, 3.83 mmol). After stirring for 60 minutes at room temperature, the precipitated salts were filtered off and washed with a further portion of THF (5 ml). The solvent was removed in vacuo to yield the crude product of a white solid that was used into the next reaction without further purification.

(b) Cis, cis-Spirodiazide: A solution of mesylate (from previous step) and sodium azide, NaN$_3$ (0.339 g, 5.2 mmol) in DMF (2.5 mL) was heated at 90° C. for 17 hrs. After cooling down to room temperature, the reaction was diluted with MTBE (50 mL) and washed with H$_2$O (5×50 mL). The organic phase was then dried (anhydrous MgSO$_4$) and concentrated under reduced pressure to afford the crude product. Flash column chromatography eluting with hexane followed by hexane-ethyl acetate (4:1) gave the cis, cis diazide. $^1$H NMR (CDCl$_3$, 400 MHz) δ 3.7 (2H, s, CH), 2.0-1.0 (6H, m, CH$_2$).

(c) C is, cis-SpiroDiamine: A mixture of the diazide (0.1 g) and Pd/C (10 wt % Pd, 0.010 g) was stirred in an autoclave under hydrogen (80 psi) for 2 hrs. The H$_2$ pressure was released and the mixture filtered through celite. The solvent was removed to give the diamine as a colourless oil. $^1$H NMR (CDCl$_3$, 400 MHz) δ 3.1 (2H, d, CH), 2.0-1.0 (6H, m, CH$_2$).

EXAMPLE 14

Preparation of Cis,Cis-Spirodiamine Catalysts a) Preparation of Ru[Cl$_2${(R)-PhanePHOS}{(cis, cis)-SpiroDiamine}]

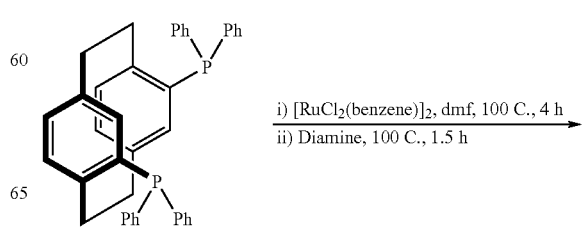

-continued

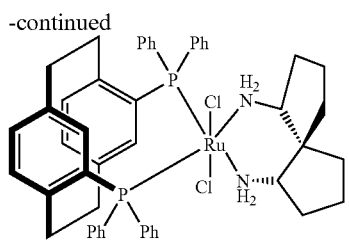

(R)-PhanePHOS (33 mg, 0.058 mmol) and [Ru(benzene)Cl]$_2$ (14.7 mg, 0.0294 mmol) were placed in a Schlenk flask and the air was replaced with nitrogen. Anhydrous, degassed DMF (1.5 ml) and toluene (2 ml) were added. The mixture was then heated at 105° C. for 4 hours. A red homogeneous solution was obtained. To the solution was then added solid cis,cis-SpiroDiamine (0.05889 mmol) and the solution heated again for 1.5 hrs at 105° C. The solvent was then removed under vacuo. The resulting solid was dissolved in CH$_2$Cl$_2$ and MTBE added. Removal of the solvent caused precipitation of a tan coloured solid. The solid was not collected but the solvent completely removed to give the crude complex, which was used without any further purification. Ru[Cl$_2${(R)-Phanephos}{(cis,cis)-SpiroDiamine}]: $^{31}$P NMR (CDCl$_3$): 44.68 ppm.

What is claimed is:

1. A chiral catalyst comprising the reaction product of a ruthenium compound, a chiral bis(phosphine) and a chiral diamine of formula (I)

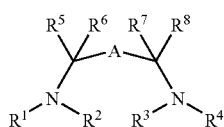

in which R$^1$, R$^2$, R$^3$ and R$^4$ are independently hydrogen, a saturated or unsaturated alkyl or cycloalkyl group, an aryl group or a urethane or sulphonyl group, R$^1$ and R$^2$ may be linked or R$^3$ and R$^4$ may be linked so as to form a 4 to 7-membered ring structure incorporating the nitrogen atom, at least one of R$^1$, R$^2$, R$^3$ and R$^4$ is hydrogen; A is a linking group consisting of one or two substituted or unsubstituted carbon atoms; R$^5$, R$^6$, R$^7$ and R$^8$ are independently hydrogen, a saturated or unsaturated alkyl or cycloalkyl group, or an aryl group, wherein one or more of R$^5$, R$^6$, R$^7$ and R$^8$ forms one or more ring structures with linking group A, and the chiral bis(phosphine) is selected from the group consisting of BINAP, DUPHOS, BIPHEP, TMBTP, BITIANAP, BIBFUP, bppm, CARBOPHOS, JOSIPHOS, BPE, DEGPHOS, DIOP, BIPNOR, PHANEPHOS, SELKE and BINAPAN.

2. The catalyst according to claim 1 wherein R$^1$, R$^2$, R$^3$ and R$^4$ are the same or different and are selected from hydrogen, methyl, ethyl, isopropyl, cyclohexyl, phenyl and 4-methylphenyl groups.

3. The catalyst according to claim 1 wherein R$^1$ and R$^2$ are linked or R$^3$ and R$^4$ are linked so as to form a 4 to 7-membered ring structure incorporating the nitrogen atom.

4. The catalyst according to claim 1 wherein the ring structure formed by one or more of R$^5$, R$^6$, R$^7$ and R$^8$ with linking group A comprises an alkyl or heteroalkyl 4- to 7-membered ring.

5. The catalyst according to claim 2 wherein the ring structure formed by one or more of R$^5$, R$^6$, R$^7$ and R$^8$ with linking group A comprises an alkyl or heteroalkyl 4- to 7-membered ring.

6. The catalyst according to claim 3 wherein the ring structure formed by one or more of R$^5$, R$^6$, R$^7$ and R$^8$ with linking group A comprises an alkyl or heteroalkyl 4- to 7-membered ring.

7. The catalyst according to claim 1 wherein the chiral diamine is of formula (III)

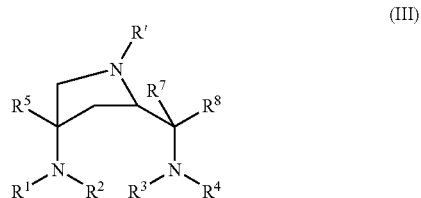

wherein R' is a protecting group.

8. The catalyst according to claim 7 wherein R$^1$, R$^2$ and R$^5$ are hydrogen, R$^3$ and R$^4$ are hydrogen or alkyl, R$^7$ and R$^8$ are hydrogen, alkyl or aryl and R' is selected from the group consisting of alkyl, aryl, carboxylate, amido and sulphonate protecting groups.

9. The catalyst according to claim 8 wherein the protecting group R' is selected from the group consisting of benzyl, methyl, tert-butyl, allyl, phenyl, substituted phenyl, CO$_2$C(CH$_3$)$_3$, CO$_2$CH$_2$C$_6$H$_5$, ethyl carbonate, formamide, acetamides, benzamides, tosyl and mesyl.

10. The catalyst according to claim 7 wherein the chiral diamine is 4-amino-2-aminomethylpyrrolidine-1-carboxylic acid tert-butyl ester (PyrBD),

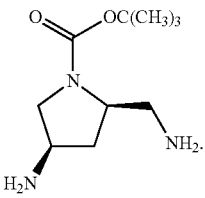

11. The catalyst according to claim 1 wherein the chiral diamine is of formula (V) wherein n=1 or 2,

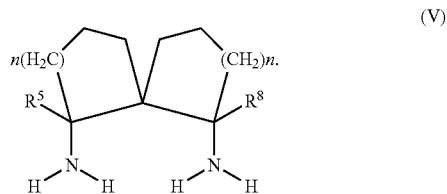

12. The catalyst according to claim 11 wherein R$^5$ and R$^8$ are hydrogen.

13. The catalyst according to claim 1 wherein the chiral bis(phosphine) is BINAP, DUPHOS or PHANEPHOS.

14. The catalyst according to claim 1 wherein the chiral bis(phosphine) is phenyl, tolyl or xylyl BINAP.

15. The catalyst according to claim 1 wherein the chiral bis(phosphine) is tol-BINAP.

16. A method of asymmetrically hydrogenating a ketone or imine, comprising contacting the ketone or imine with a catalyst according to claim 1.

17. The method of claim 16, wherein the ketone or imine is an alkyl ketone of formula RCOR' in which R and R' are substituted or unsubstituted, saturated or unsaturated C1-C20 alkyl or cycloalkyl which may be linked and form part of a ring structure.

* * * * *